United States Patent [19]

Egerton

[11] Patent Number: 4,831,017
[45] Date of Patent: May 16, 1989

[54] INCREASED LITTER SIZE IN MONOGASTRIC DOMESTIC ANIMALS AFTER TREATMENT IN MID-GESTATION OF GRAVID FEMALE WITH AVERMECTIN OR MILBEMYCIN COMPOUND

[75] Inventor: John R. Egerton, Neshanic Station, N.J.

[73] Assignee: Merck & Co., Inc., Rahway, N.J.

[21] Appl. No.: 67,569

[22] Filed: Jun. 29, 1987

[51] Int. Cl.$^4$ .............................................. A61K 31/70
[52] U.S. Cl. ....................................................... 514/30
[58] Field of Search ........................................... 514/30

[56] References Cited

U.S. PATENT DOCUMENTS

| | | | |
|---|---|---|---|
| Re. 32,006 | 10/1985 | Chabala et al. | 549/264 |
| Re. 32,034 | 11/1985 | Chabala et al. | 549/260 |
| 3,950,360 | 4/1976 | Aoki et al. | 424/279 X |
| 4,199,569 | 4/1980 | Chabala et al. | 424/180 |
| 4,201,861 | 5/1980 | Mrozik et al. | 536/17 A |
| 4,206,205 | 6/1980 | Mrozil et al. | 424/180 |
| 4,310,519 | 1/1982 | Albers-Schonberg et al. | 424/181 |
| 4,378,353 | 3/1983 | Goegelman et al. | 424/181 |
| 4,427,663 | 1/1984 | Mrozik et al. | 424/180 |
| 4,547,520 | 10/1985 | Ide et al. | 514/450 |

*Primary Examiner*—Frederick E. Waddell
*Attorney, Agent, or Firm*—David L. Rose; Michael C. Sudol

[57] ABSTRACT

Novel method of increasing litter size in monogastric domestic animals by administering an avermectin or milbemycin compound during mid-gestation.

14 Claims, No Drawings

INCREASED LITTER SIZE IN MONOGASTRIC DOMESTIC ANIMALS AFTER TREATMENT IN MID-GESTATION OF GRAVID FEMALE WITH AVERMECTIN OR MILBEMYCIN COMPOUND

BACKGROUND OF THE INVENTION

Avermectin and milbemycin compounds are known for having superior anthelmintic and antiparasitic effects. For example, see U.S. Pat. Nos. 4,310,519 to Albers-Schonberg et al., 4,378,353 to Goegelman et al. and 4,199,569 to Chabala et al. which disclosed avermectin compounds and 3,950,360 to Aoki et al. which disclosed milbemycin compounds. The use of said compounds is growing parasitised animals generally results in a weight increase being due to the general improvement of the health of said animals as the parasite burden is reduced. These known compounds have been found to possess a novel utility by reducing the transmission of certain infectious disease organisms prior to and after birth and increasing litter size in monogastric domestic animals after treatment about mid-gestation of gravid female with said compounds.

SUMMARY OF THE INVENTION

It has been observed that avermectin and milbemycin compounds have a significant effect in reducing the transmission of certain infectious disease organisms. It has been further observed that avermectin and milbemycin compounds increase litter size when administered to gravid female animals in mid-gestation. Therefore, it is an object of this invention to describe the observed and unexpected increases in litter size of pregnant animals which had been treated mid-gestationally with avermectin or milbemycin compounds.

A further object of this invention is to describe formulations useful in administering an avermectin or milbemycin compound as an active agent for increased litter size.

Further objects will become apparent from the description which follows.

DESCRIPTION OF THE INVENTION

Avermectin compounds have been discovered to have significant antiparasitic effects in animals. The compounds of this invention include the eight avermectin natural products described in U.S. Pat. No. 4,310,519 to Albers-Schonberg et al. and a series of semisynthetic compounds derived therefrom and including various members of the milbemycins. The natural avermectins are isolated from a fermentation broth as four pairs of compounds and the pair identified as Bla/Blb is the most preferred. The 22,23-dihydro derivatives of the avermectins are disclosed in U.S. Pat. No. 4,199,569 to Chabala et al. and the 22,23-dihydro avermectin Bla/Blb pair of compounds in an approximate 80:20 mixture is preferred and known as ivermectin.

Other avermectin derivatives such as monosaccharide and aglycone derivatives disclosed in U.S. Pat. No. 4,206,205 to Mrozik et al., the acylated derivatives thereof such as those disclosed in U.S. Pat. No. 4,201,861 to Mrozik et al., the 13-deoxy aglycone compounds disclosed in U.S. Pat. No. Re. 32,034 and U.S. Pat. No. Re. 32,006, and the 4"-keto and 4"-amino compounds disclosed in U.S. Pat. No. 4,427,663 to Mrozik are useful as litter size enhancing agents.

The preferred avermectin compounds employed in the practice of this invention are realized in the following structural formula:

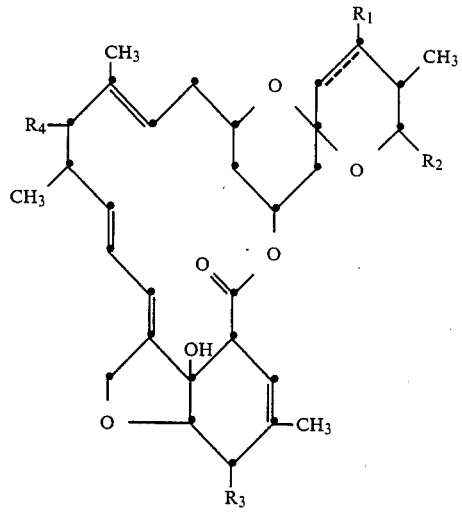

wherein the broken line indicates a single or double bond at the 22,23-position;

$R_1$ is H, =O, loweralkanoyloxy or OH, provided that $R_1$ is present only when the broken line indicates a single bond;

$R_2$ is methyl, ethyl, isopropyl or sec-butyl;

$R_3$ is OH, $OCH_3$ or loweralkanoyloxy;

$R_4$ is H, OH, loweralkanoyloxy, α-L-oleandrosyloxy, 4'-(α-L-oleandrosyl)-α-L-oleandrosyloxy, 4'-loweralkanoyl-α-L-oleandrosyloxy, 4"-loweralkanoyl-4'-(α-L-oleandrosyl)-α-L-oleandrosyloxy, 4"-amino-4'-(α-L-oleandrosyl)-α-L-oleandrosyloxy, 4"-mono- or diloweralkylamino-4'-(α-L-oleandrosyl)-α-L-oleandrosyloxy, and physiologically acceptable salts thereof.

Additional compounds usable as litter size enhancing agents are the milbemycin compounds disclosed in U.S. Pat. No. 3,950,360 to Aoki et al. and the oxime derivatives thereof disclosed in U.S. Pat. No. 4,547,520 to Ide et al.

The preferred milbemycin compounds employed in the practice of this invention are realized in the following formula:

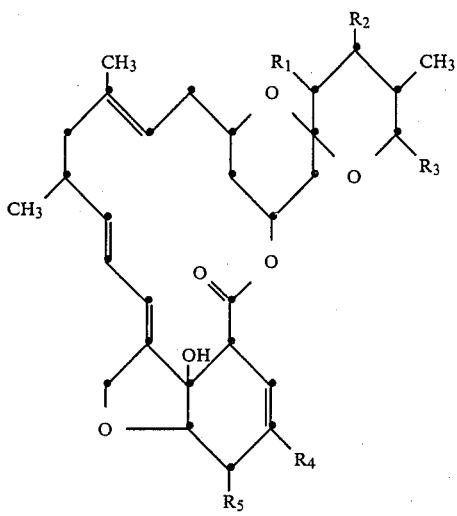

wherein the various R groups have the following meanings:

| $R_1$ | $R_2$ | $R_3$ | $R_4$ | $R_5$ |
|---|---|---|---|---|
| H | H | $CH_3$ | $CH_3$ | OH |
| H | H | $CH_3$ | $CH_3$ | $OCH_3$ |
| H | H | $C_2H_5$ | $CH_3$ | OH |
| H | H | $C_2H_5$ | $CH_3$ | $OCH_3$ |
| OH | $-O-\overset{O}{\underset{\|\|}{C}}-\overset{CH_3}{\underset{\|}{CH}}-C_4H_9$ | $CH_3$ | $CH_3$ | OH |
| OH | $-O-\overset{O}{\underset{\|\|}{C}}-\overset{CH_3}{\underset{\|}{CH}}-C_4H_9$ | $CH_3$ | $CH_3$ | $OCH_3$ |
| OH | $-O-\overset{O}{\underset{\|\|}{C}}-\overset{CH_3}{\underset{\|}{CH}}-C_4H_9$ | $C_2H_5$ | $CH_3$ | OH |
| OH | $-O-\overset{O}{\underset{\|\|}{C}}-\overset{CH_3}{\underset{\|}{CH}}-C_4H_9$ | $C_2H_5$ | $CH_3$ | $OCH_3$ |
| H | H | $CH_3$ | $-CH_2-OC(O)-\text{(pyrrole)}$ | OH |
| H | H | $C_2H_5$ | $-CH_2-OC(O)-\text{(pyrrole)}$ | OH |
| H | H | $i-C_3H_7$ | $-CH_2-OC(O)-\text{(pyrrole)}$ | OH |
| H | H | $CH_3$ | $CH_3$ | $=N-OR_6$ |
| H | H | $C_2H_5$ | $CH_3$ | $=N-OR_6$ |
| H | H | $i-C_3H_7$ | $CH_3$ | $=N-OR_6$ | wherein $R_6$ is hydrogen or loweralkyl.

The term "loweralkyl" when used in the instant application is intended to represent those alkyl groups either straight or branched chain which have from 1–5 carbon atoms. Examples of such alkyl groups are methyl, ethyl, propyl, iso-propyl, butyl, sec-butyl, pentyl, and the like.

The term "loweralkanoyl" is intended to include those alkanoyl groups containing from one to five carbon atoms in either a straight or branched chain. Examples of such alkanoyl groups are formyl, acetyl, propionyl, butyryl, valeryl, and the like.

While it is certainly feasible, it is generally unnecessary to separate the "b" compounds, those with a 25-isopropyl group, from the corresponding "a" compounds with a 25-sec-butyl group and as such the compounds are generally isolated as mixtures of the two compounds. Thus references in the instant application to "a" compounds such as B1a, A1a, and the like, are construed to define the pure compound as well as those which actually contain a certain proportion of the corresponding "b" compound. Alternatively, this representation of a mixture is sometimes done by referring to the B1 or B2 compounds or by separating the "a" compound from the "b" compound by a slash (/) such as B1a/B1b, B2a/B2b and the like.

The avermectin and milbemycin compounds disclosed herein are useful in treating certain infectious diseases in ruminant and non-ruminant animals such as sheep, cattle, goats, horses, swine, chickens and the like and in addition thereto, are specifically useful for increasing litter size in monogastric domestic animals by administering said compounds at or about mid-gestation. The active compound can be administered to the animal by incorporating it into the animal's feed or drinking water or in a unit dosage form either parenterally or enterally as, for example, a topical liquid, drench, tablet, bolus or sustained release bolus, injection, or subcutaneous implant. The administration of said active compounds produces a surprising increase in litter size.

The active compounds can be administered to animals at daily rates of from 0.02 to 2.0 mg/kg of body weight which may vary depending upon the particular animal being treated as well as the age and general physical condition of the animal. Preferably, daily dosages of from 0.1 to 1.0 mg/kg are utilized. When administered as part of the animal's feed or drinking water the active compound is present at rates of from 0.1 to 100 ppm which is determined to provide the appropriate daily amounts of the active compound.

The compounds are administered approximately midway through the pregnancy, however, successful results can be achieved when the active compound is administered approximately at from 20 to 70 percent of the complete term. Preferably the active compound is administered approximately at from 23 to 39 percent of the gestational period. Thus, for example a dog with an average gestational period of about 65 days, the compound would be administered at approximately between 15 and 45 days of the pregnancy, preferably between 15 and 25 days. For a pig with a gestation period of about 112 days the active compound would be administered at approximately between 23 and 79 days, preferably between 25 and 44 days of the pregnancy.

Administration of the active compound is generally carried out for about 1 to 5 days during the above administration period, preferably for about 2 to 3 days. The compounds may be administered on sequential days or days of administration may be alternated with one or more non-treatment days The compounds which increase litter size disclosed herein have been demonstrated in bitches given 0.6 (0.2×3), 1.0 (0.5×2) for a 2–3 day period and 1.0 (1.0×1) mg/kg.

Some studies which further exemplify the concepts of this invention are shown below.

Prophylaxis of *Toxocara canis* and *Ancylostoma caninum* via treatment of the infected gravid bitch and said treatment's effect upon litter size and survivability of the whelps The mean number of *Toxocara canis* transmitted from dam to pup in the three ivermectin treated levels listed above was not statistically significantly (P>0.05) different from the mean number of *T. canis* transmitted from placebo (control) treated dams to their pups when ivermectin treatments were administered on or about mid-gestation. On the contrary, all three ivermectin experimental prophylactic protocols successfully reduced the transmission of *Ancylostoma caninum* (p<0.05) with one protocol, 0.5 mg/kg×2 S.C, nearly eliminating (p<0.01) hookworm infection entirely. It was strongly indicated (p<0.05) that litter size was larger in bitches administered ivermectin S.C. at 0.5 mg/kg×2 or (p<0.1) at 1.0 mg/kg×1 than was the litter size for placebo administered bitches; the effect on litter size was not dependent upon which of two breeding studs was utilized (p>0.75).

Twelve yound cross-bred bitches of breeding age were bred to one of two studs, depending upon respective genetic backgrounds, at the first sign of estrus and according to the breeding protocol given below.

The day a bitch shows signs of estrus (swollen vulva, red vaginal discharge) she should be selected for breeding. The bitch is to be bred by an appropriate stud. The first time the bitch stands (accepts) for the stud and copulation occurs is to be considered day 1. Breeding should be continued on subsequent alternate days (Day 3, 5, 7) for 4 consecutive breedings if possible although 3 or 2 breedings will be acceptable. Breeding dates are to be recorded for each bitch.

When bitch accepts stud 1st time is Day 1-skip Day 2
Breed 2nd time Day 3-skip Day 4
Breed 3rd time Day 5-skip Day 6
Breed 4th time (if she accepts) on Day 7-End.

At the third mating (gestation Day 0) each bitch was inoculated with 20,000 larvated *T. canis* eggs P.O. and 20,000 $L_3$ *A. caninum* S.C. As each bitch was infected in sequence she was assigned from three contiguous blocks (replicates) of four bitches to one of 4 prophylactic protocols at random: (1) placebo vehicle, S.C.; (2) ivermectin micelle 0.2. mg/kg S.C., on Day 17, 20, 23; (3) ivermectin micelle at 0.5 mg/kg, S.C., on Day 18, 22; and (4) ivermectin micelle at 1.0 mg/kg, S.C., on Day 20. Accession to the three contiguous blocks was on the date of first breeding.

During gestation the bitches were maintained under sound but ordinary conditions of care with no extraordinary intervention through whelping and weaning. Litter sizes were recorded at whelping and deaths to weaning were recorded for each of the twelve litters whelped. All pups dying prior to weaning were examined in toto for enteral and parenteral *T. canis* and *A. caninum*. At weaning (9 weeks post-whelping) surviving pups of each litter were euthanized and examined for enteral parasites in toto; parenteral parasites present in either case were determined from quantitative organ/tissue samples subjected to artificial digestion with 1% HCl:0.7% pepsin solution.

Analysis of worm counts for both *T. canis* and *A. caninum* was done on $\log_{10}$ transformed counts using the bitch as the experimtal unit, i.e., the geometric mean for all pups surviving to weaning in a given litter, by parasite species, was the single datum per replication for analysis. Litter size and survivability were analyzed by pup count, both total number whelped and number surviving to weaning, by analysis of variance, by $x^2$ for expectation and by Fisher's Exact test, as appropriate. Litter size and survivability of pups, within breeding stud, were similarly analyzed.

TABLE 1

Effect of ivermectin treatment of the gravid bitch on the mean number of *Toxocara canis* harbored by their pups at weaning.

| Treatment | # of Bitches | T. canis/pup, weaning Geom. Mean[a] | $\log_{10}$ Mean ± $\log_{10}$ S.E. |
|---|---|---|---|
| Placebo (Control) | 3 | 11.4 | 1.0565 ± 0.0468 |
| 0.2 mg/kg × 3, S.C.[b] | 3 | 10.4 | 1.0168 ± 0.2079 |
| 0.5 mg/kg × 2, S.C.[c] | 3 | 6.1 | 0.7887 ± 0.3846 |

TABLE 1-continued

Effect of ivermectin treatment of the gravid bitch on the mean number of *Toxocara canis* harbored by their pups at weaning.

| Treatment | # of Bitches | T. canis/pup, weaning | |
|---|---|---|---|
| | | Geom. Mean[a] | $\log_{10}$ Mean ± $\log_{10}$ S.E. |
| 1.0 mg/kg × 1, S.C.[d] | 3 | 12.2 | 1.0854 ± 0.0603 |

[a] of litter means within treatment.
[b] Rx on days 17, 20 and 23 of gestation.
[c] Rx on days 18 and 22 of gestation.
[d] Rx on day 20 of gestation.

There was no substantive effect of any treatment protocol upon the transuterine plus post-partum transmission of *T. canis* from bitch to pup.

TABLE 2

Effect of ivermectin treatment of the gravid bitch on the mean number of *Ancylostoma caninum* harbored by their pups at weaning.

| Treatment | # of Bitches | A. caninum/pup, weaning | |
|---|---|---|---|
| | | Geom. Mean[a] | $\log_{10}$ Mean ± $\log_{10}$ S.E. |
| Placebo (Control) | 3 | 128.8 | 2.1098 ± 0.0702 |
| 0.2 mg/kg × 3, S.C.[b] | 3 | 27.0* | 1.4317 ± 0.2920 |
| 0.5 mg/kg × 2, S.C.[c] | 3 | 0.3**Ob | −0.4380 ± 0.5121 |
| 1.0 mg/kg × 1, S.C.[d] | 3 | 5.7* | 0.7535 ± 0.2677 |

[a,b,c,d] See Table 1.
*Difference from control value due to treatment, $p < 0.05$
**Difference from control value due to treatment, $p < 0.01$
O Superior to treatment at 1.0 mg/kg × 1, $p < 0.05$
b Superior to treatment at 0.2 mg/kg × 3, $p < 0.01$ There was a marked effect of treatment using any of the three experimental protocols upon the post-partum transmission of *A. caninum* from bitch to pup, the most effective one being 0.5 mg/kg × 2, S.C., on the 18th and 22nd gestation day followed rather closely by 1 mg/kg, S.C., on the 20th day of gestation.

These prophylatic ivermectin applications reduced the at-weaning hookworm populations by >99 and 96%, respectively.

TABLE 3

Effect of ivermectin treatment of the gravid bitch on the size of litter whelped.

| Treatment | Number of Bitches | Pups/litter (total) (Mean ± S.E.) |
|---|---|---|
| Placebo (Control) | 3 | 5.3 ± 2.33 |
| 0.2 mg/kg × 3, S.C.[b] | 3 | 3.3 ± 1.20 |
| 0.5 mg/kg × 2, S.C.[c] | 3 | 9.7* ± 1.20 |
| 1.0 mg/kg × 1, S.C.[d] | 3 | 7.0 ± 0.58 |

[b], [c], and [d] See Table 1.
*Mean litter size greater than for placebo and 0.2 mg/kg × 3 treatments, pZ0.05; 0.5 mg/kg × 2 and 1.0 mg/kg × 1 treatment group means comparable, $p > 0.05$.

An unexpected result is shown in Table 3. Ivermectin treatment of the gravid bitch with either 0.5 mg/kg × 2 or 1.0 mg/kg × 1 resulted in significantly larger litters of pups ($p < 0.05$ and $p < 0.1$, respectively). Because 2 separate stud dogs were used during this breeding experiment (genetic considerations) the expectation for litter size was examined between the studs.

TABLE 4

Comparison of total and surviving pups per litter sired by each of two studs.

| Total Pups/Litter | Surviving Pups/Litter |
|---|---|
| $x^2 = 0.046$ | $x^2 = 0.018$ |
| $P > 0.8$ | $P > 0.8$ |

P = Probability of no difference in number of pups/litter from two separate studs; 6 litters/stud.

Expectations for number of pups per litter, for both total pups whelped and number of pups surviving to weaning, did not deviate from normal expectation within studs when examined across bitches and treatment protocols. It can be concluded that the differences in mean litter size were dependent upon specific ivermectin treatments and not upon the particular sire. What is more, as the predominantly prenatally acquired *T. canis* infections were not significantly affected by treatment (Table 1), it cannot be argued that the control of that parasite solely influenced litter size. As *A. caninum*, which was well controlled by ivermectin treatment of the bitch (80→99%), was only acquired via transmammary transmission post-natally, it cannot be argued that control of that parasite was solely responsible for the significant increase in litter size. The rational deduction thus becomes that ivermectin, per se, had a pharmacological effect upon the bitch at mid-gestation which resulted in larger litters when administered according to the 0.5 mg/kg × 2 or 1.0 mg/kg × 1 protocols.

What is claimed is:

1. A method for increasing the surviving litter size in mongastric domestic animals which comprises administering to said animals during mid-gestation an effective amount of an avermectin or milbemycin compound.

2. the method of claim 1 wherein said active compound has the formula:

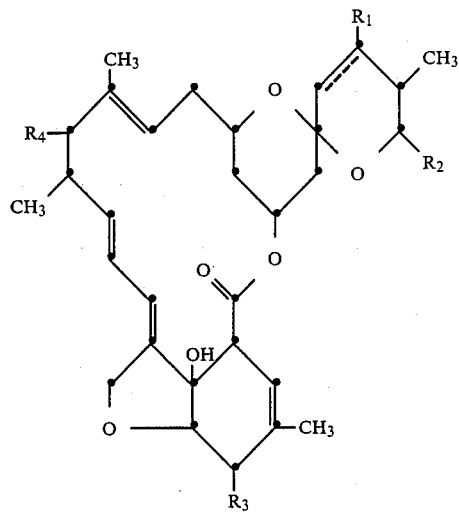

wherein the broken line indicates a single or double bond at the 22,23-position;
$R_1$ is H, =O, loweralkanoyloxy or OH, provided that $R_1$ is present only when the broken line indicates a single bond;
$R_2$ is methyl, ethyl, isopropyl or sec-butyl;
$R_3$ is OH, OCH$_3$ or loweralkanoyloxy;
$R_4$ is H, OH, loweralkanoyloxy, α-L-oleandrosyloxy, 4'-(α-L-oleandrosyl)-α-L-oleandrosyloxy, 4'-loweralkanoyl-α-L-oleandrosyloxy, 4''-loweralkanoyl-4'-(α-L-oleandrosyl)-α-L-oleandrosyloxy, 4''-amino-4'-(α-L-oleandrosyl)-α-L-oleandrosyloxy, 4''-mono- or diloweralkylamino-4'-(α-L-oleandrosyl)-α-L-oleandrosyloxy,
and physiologically acceptable salts thereof.

3. The method of claim 2 wherein said active compound is ivermectin.

4. The method of claim 1 wherein the active compound has the formula:

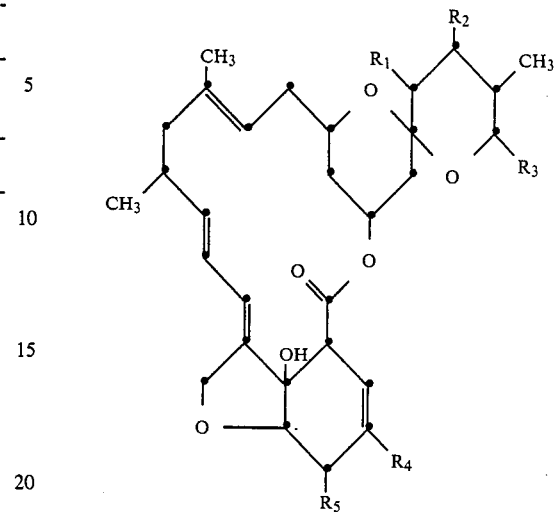

wherein the various R groups have the following meanings:

| $R_1$ | $R_2$ | $R_3$ | $R_4$ | $R_5$ |
|---|---|---|---|---|
| H | H | $CH_3$ | $CH_3$ | OH |
| H | H | $CH_3$ | $CH_3$ | $OCH_3$ |
| H | H | $C_2H_5$ | $CH_3$ | OH |
| H | H | $C_2H_5$ | $CH_3$ | $OCH_3$ |
| OH | $-O-\overset{O}{\underset{\parallel}{C}}-\overset{CH_3}{\underset{\mid}{CH}}-C_4H_9$ | $CH_3$ | $CH_3$ | OH |
| OH | $-O-\overset{O}{\underset{\parallel}{C}}-\overset{CH_3}{\underset{\mid}{CH}}-C_4H_9$ | $CH_3$ | $CH_3$ | $OCH_3$ |
| OH | $-O-\overset{O}{\underset{\parallel}{C}}-\overset{CH_3}{\underset{\mid}{CH}}-C_4H_9$ | $C_2H_5$ | $CH_3$ | OH |
| OH | $-O-\overset{O}{\underset{\parallel}{C}}-\overset{CH_3}{\underset{\mid}{CH}}-C_4H_9$ | $C_2H_5$ | $CH_3$ | $OCH_3$ |
| H | H | $CH_3$ | $-CH_2-O\overset{O}{\underset{\parallel}{C}}\!\!-\!\!\underset{\underset{H}{\mid}{N}}{\text{pyrrole}}$ | OH |
| H | H | $C_2H_5$ | $-CH_2-O\overset{O}{\underset{\parallel}{C}}\!\!-\!\!\underset{\underset{H}{\mid}{N}}{\text{pyrrole}}$ | OH |
| H | H | i-$C_3H_7$ | $-CH_2-O\overset{O}{\underset{\parallel}{C}}\!\!-\!\!\underset{N}{\text{pyrrole}}$ | OH |
| H | H | $CH_3$ | $CH_3$ | $=N-OR_6$ |
| H | H | $C_2H_5$ | $CH_3$ | $=N-OR_6$ |
| H | H | i-$C_3H_7$ | $CH_3$ | $=N-OR_6$ | wherein $R_6$ is hydrogen or loweralkyl.

5. The method of claim 4 wherein:

| R₁ | R₂ | R₃ | R₄ | R₅ |
|----|----|------|------|------|
| H | H | CH₃ | CH₃ | OH |
| H | H | CH₃ | CH₃ | OCH₃ |
| H | H | C₂H₅ | CH₃ | OH |
| H | H | C₂H₅ | CH₃ | OCH₃. |

6. The method of claim 5 wherein:

| R₁ | R₂ | R₃ | R₄ | R₅ |
|----|----|------|------|------|
| H | H | CH₃ | CH₃ | OH |
| H | H | C₂H₅ | CH₃ | OH. |

7. The method of claim 1 wherein said active compound is administered at a dosage of from 0.02 to 2.0 mg/kg/day of the animal's body weight.

8. The method of claim 7 wherein said active compound is administered at a dosage of from 0.1 to 1.0 mg/kg/day of the animal's body weight.

9. The method of claim 1 wherein said active compound is parenterally administered.

10. The method of claim 9 wherein said active compound is administered subcutaneously.

11. The method of claim 1 wherein the active compound is administered during the period for 20 to 70 percent of the duration of the pregnancy.

12. The method of claim 11 wherein the active compound is administered during the period for 23 to 39 percent of the duration of the pregnancy.

13. The method of claim 1 wherein the administration of the active compound is carried out for about 1 to 5 days either sequentially or alternated with one or more non-treatment days.

14. The method of claim 13 wherein the administration is carried out for about 2 to 3 days.

* * * * *